US006238426B1

United States Patent
Chen

(10) Patent No.: US 6,238,426 B1
(45) Date of Patent: May 29, 2001

(54) REAL-TIME MONITORING OF PHOTODYNAMIC THERAPY OVER AN EXTENDED TIME

(75) Inventor: James C. Chen, Bellevue, WA (US)

(73) Assignee: Light Sciences Corporation, Issaquah, WA (US)

( * ) Notice: Subject to any disclaimer, the term of this patent is extended or adjusted under 35 U.S.C. 154(b) by 0 days.

(21) Appl. No.: 09/356,938

(22) Filed: Jul. 19, 1999

(51) Int. Cl.$^7$ .................................................. A61N 5/06
(52) U.S. Cl. .............................. 607/88; 607/91; 607/92; 359/201; 606/10; 606/11; 606/12
(58) Field of Search ............................... 607/88, 89, 92, 607/98, 99; 606/9, 13–16; 128/898

(56) References Cited

U.S. PATENT DOCUMENTS 5,354,323 * 10/1994 Whitebook ............................. 607/89
5,464,436 * 11/1995 Smith ..................................... 607/89

(List continued on next page.)

OTHER PUBLICATIONS

Wilson et al., "Monitoring tissue response to photodynamic therapy: The potential of minimally invasive electrical impedance spectroscopy and high–frequency ultrasound" SPIE. vol. 3592. Jan. 1999, pp. 73–82.*

Finger et al., "Use of Scanning Doppler Velocimetry to monitor vascular changes during Photodynamic Therapy." SPIE. vol. 3592. Jan. 1999.*

Brasseur, Nicole; Lewis, Karina; Rousseau, Jacques; and Van Lier, Johan E. "Measurement of Tumor Vascular Damage in Mice with $^{99m}$Tc–MIBI Following Photodynamic Therapy." Photochemistry and Photobiology, 1996, 64(4): 702–706.

Bruce, Charles J.; Packer, Douglas L.; and Seward, James B. "Intracardiac Doppler Hemodynamics and Flow: New Vector, Phased–Array Ultrasound–Tipped Catheter." The American Journal of Cardiology. vol. 83. May 15, 1999. pp. 1509, 1511–1512.

Delorme, S.; and Knopp, M. V. "Non–invasive vascular imaging: assessing tumour vascularity." Review Article. European Radiology. vol. 8. 1998. pp. 517–527.

(List continued on next page.)

Primary Examiner—John Mulcahy
Assistant Examiner—Ahmed Farah
(74) Attorney, Agent, or Firm—Ronald M. Anderson

(57) ABSTRACT

Progress of photodynamic therapy (PDT) administered over an extended period of time is monitored using an ultrasonic probe, which produces ultrasound images of an internal treatment site in real time. The ultrasound images indicate the extent and volume of an infarction zone within a tumor or other diseased tissue at the internal treatment site within a patient's body. Light is administered to the internal treatment site from either an internal or external light source that produces light in a waveband corresponding to the characteristic absorption waveband a photoreactive agent that is administered to a patient. Prior to or shortly after initiating administration of the light therapy, a baseline ultrasound image is produced for comparison to subsequent ultrasound images made after the effects of the PDT on the diseased tissue have occurred. By evaluating changes in the internal treatment site shown in the ultrasound images during the progress of the PDT, the intensity and/or duration of intervals of light being administered to the patient can be varied, and/or terminated at an appropriate time, thereby minimizing risk of harm to normal tissue surrounding the internal treatment site. Light is delivered from an external laser source through an optical fiber, or through an implanted light probe that includes one or more light emitting sources, or by an external array of light emitting diodes that emit light of sufficiently long wavelength to penetrate a dermal layer into the internal treatment site.

44 Claims, 4 Drawing Sheets

U.S. PATENT DOCUMENTS

| | | | |
|---|---|---|---|
| 5,474,528 | 12/1995 | Meserol | 604/20 |
| 5,527,349 | 6/1996 | Landry et al. | 607/88 |
| 5,571,151 | 11/1996 | Gregory | 607/88 |
| 5,586,982 * | 12/1996 | Abela | 606/28 |
| 5,707,403 * | 1/1998 | Grove et al. | 607/89 |

OTHER PUBLICATIONS

Desinger, K.; Liebold, K.; Helfmann, J.; Stein, T.; and Müller, G. "A new system for a combined laser and ultrasound application in neurosurgery." Neurological Research. vol. 21. Jan. 1999. pp. 84–88.

Fingar, Victor H.; Wieman, Jeffery T.; Taber, Scott W.; Singh, Pavan; Kempf, Jr.; Stephen J.; Pietsch, Cathy G.; and Maldonado, Claudio. "Use of Scanning Doppler Velocimetry to monitor vascular changes during Photodynamic Therapy." Invited Paper. SPIE. vol. 3592. Jan. 1999. pp. 14–19.

Meyerowitz, Colin B.; Fleischer, Arthur C.; Pickens, David R.; Thurman, Gary B.; Borowsky, Alexander D.; Thirsk, Graham; and Hellerqvist, Carl G. "Quantification of Tumor Vascularity and Flow with Amplitude Color Doppler Sonography in an Experimental Model: Preliminary Results." J Ultrasound Med 15:827–833, 1996.

Moore, R.B.; Chapman, J.D.; Mokrzanowski, A.D.; Arnfield, M.R.; McPhee, M.S.; and McEwan, A.J. "Non–invasive monitoring of photodynamic therapy with $^{99}$Technetium HMPAO scintigraphy." Br. J. Cancer, vol. 65. 1992. pp. 491–497.

Sakarya, M.E.; Arslan, H.; Unal, O.; Atilla, M.K.; and Aydin, S. "The role of power Doppler ultrasonograpy in the diagnosis of prostate cancer: a preliminary study." British Journal of Urology. vol. 82. 1998. pp. 386–388.

Tanaka, Sachiko; Kitamura, Tsugio; Fujita, Makoto; Nakanishi, Katsumi; and Okuda, Shigeru. Color Doppler Flow Imaging of Liver Tumors. AJR: 154. Mar. 1990. pp. 509–514.

Whitelaw, D.; Lees, W.; Ripley, P. Hatfield, A.; Gillams, A.; and Bown, S. Photodynamic Therapy for pancreatic cancer–a clinical pilot study. Abstract. No. P39. International Photodynamic Association. $7^{th}$ Biennial Congress. Jul. 1998.

Wilson, B.C.; Molckovsky, A.; Czarnota, G.J.; Sherar, M.D.; Kolios, M.C.; Lilge, L.; Dattani, R.S.; Osterman, K.S.; Paulsen, K.D.; and Hoopes, P.J. "Monitoring tissue response to photodynamic therapy: The potential of minimally invasive electrical impedance spectroscopy and high–frequency ultrasound." Invited Paper. SPIE vol. 3592. Jan. 1999. pp. 73–82.

* cited by examiner

REAL-TIME MONITORING OF PHOTODYNAMIC THERAPY OVER AN EXTENDED TIME

FIELD OF THE INVENTION

This invention generally relates to the use of an ultrasonic transducer to monitor the status of an internal diseased tissue, and more specifically, to monitoring the condition of an internal treatment site during the course of medical treatment administered to the site.

BACKGROUND OF THE INVENTION

Photodynamic therapy (PDT) has been shown to be very effective in destroying diseased tissue and tumors using light that is absorbed by a photoreactive agent previously administered to a patient. The photoreactive agent is selectively preferentially absorbed by or linked to abnormal or diseased tissue and has a characteristic absorption waveband to which the waveband of the light administered to the patient corresponds. When activated by the light, the photoreactive agent produces compounds, such as singlet oxygen, that destroy the abnormal tissue.

While much of the earlier work in PDT has been directed to treating surface lesions, perhaps a much more important application is in destroying internal tumors within the body of a patient. PDT may be administered interstitially using light from an external laser that is coupled to a plurality of optical fibers. The optical fibers convey the light into a tumor mass within a patient's body; however, interstitial PDT has been used preclinically and clinically on only a very limited basis. The clinical application of interstitial PDT to oncology has been associated with several significant problems, including inadvertent damage to normal tissue, tumor regrowth, lack of efficacy, and surgical risk related to surgical emplacement of multiple optical fibers to assure adequate light delivery to relatively large tumor masses. The damage to normal tissue can occur during PDT and can be highly variable due to the non-homogeneous distribution of the photoreactive agent within a tumor and within normal tissue surrounding a tumor, and differences in the intensity and penetration depth of light into heterogeneous tumor tissue. Portions of a tumor may be destroyed, while other portions survive and remain viable, leading to tumor cell repopulation and regrowth of the tumor mass. Unintended destruction of normal tissue can have serious consequences, which is contrary to the intended goal of completely destroying the tumor, while sparing the normal tissue.

Monitoring tumor fluorescence has been suggested in the prior art as a possible way to determine the border of a tumor relative to normal tissue before beginning to administer PDT. However, there is no teaching in this prior art of monitoring the effect of PDT in real time to assess its progress in destroying diseased tissue nor any teaching of how to determine the effects of light distribution in a tumor. Other methods that have been proposed to monitor a tumor's condition include using radioactive-labeled agents to monitor blood flow in vessels supplying the tumor. These methods suffer from lack of repeatability, poor resolution at a boundary between a tumor and normal tissue, and inconvenient image capture. To implement such methods, it is typically necessary to transport a patient to specially fitted suites in which the imaging equipment is installed or to move relatively large imaging devices into the proximity of the patient. Also, toxicity due to repeated injection of radionuclides into a patient is a concern, since once an injected radionuclide is trapped within thrombosed and occluded vessels at the treatment site, there is no practical method to rapidly clear the trapped radionuclide material for another injection, in order to asses further vessel shut-down.

Thus, no practical method is disclosed in the prior art for real-time monitoring of interstitial PDT in order to assess the changing extent of tumor destruction and to avoid damage to surrounding normal tissue as the treatment progresses. Typically, since the photoreactive agent is administered to a patient as a bolus so that its concentration within the patient's body cannot thereafter be controllably varied other than by giving additional doses, the only available control in administering PDT is in regard to the light intensity, duration of light administered, the timing of light administered, and the total light dose administered to a treatment site. It would therefore be desirable to develop a technique for providing PDT that enables real-time monitoring of an internal treatment site, so that one or more of these parameters can be varied in response to changes in the treatment site as the PDT continues. Such a method would allow practical, cost-effective, and non-invasive determination of the effects of the PDT on a tumor at a treatment site and its progress in destroying the tumor, and would provide guidance in varying one or more of the parameters noted above to achieve a substantial clinical benefit at minimal risk to the patient.

SUMMARY OF THE INVENTION

In accord with the present invention, a method is defined for administering light therapy to diseased tissue at an internal treatment site within a patient's body for an extended period of time, wherein the light therapy is modified in response to a condition of the internal treatment site. The method includes the step of providing a light source that emits light within a predetermined waveband. A photoreactive agent having a characteristic light absorption waveband that corresponds to the predetermined waveband in which light is emitted by the light source is administered to the patient. Subsequently, light is administered to the diseased tissue with the light source, and the light therapy continues over the extended period of time. At a plurality of times, including at least one time after an onset of administering the light, the internal treatment site is ultrasonically scanned to produce a plurality of images, each image indicating a condition of the internal treatment site at that time. By comparing an image of the internal treatment site made at a time after the onset of administering the light therapy with an image made at an earlier time, changes in the condition of the internal treatment site are detected. The light therapy is then modified in response to a change in the internal treatment site that has been thus detected.

The step of ultrasonically scanning preferably includes the step of scanning the internal treatment site before the onset of administering the light therapy, to produce a baseline image of the diseased tissue at the internal treatment site before the diseased tissue has experienced any effect from the light therapy. To determine a change in the internal treatment site, the baseline image is compared with a subsequent image made a substantial time after the onset of administering the light therapy. Alternatively, the internal treatment site can be scanned before a substantial amount of light therapy has been administered, to produce a quasi-baseline image of the diseased tissue at the internal treatment site before the diseased tissue has been substantially affected by the light therapy. In this case, the change in the internal treatment site is determined by comparing the quasi-baseline image with a subsequent image made a substantial time after the onset of administering the light therapy.

In one embodiment of the present invention, the light source preferably comprises a probe in which at least one light source is disposed and which is adapted to be interstitially inserted within the diseased tissue at the internal treatment site. Alternatively, the light source comprises an optical fiber having a distal end adapted to be interstitially inserted into the diseased tissue and thus able to convey light into the treatment site from a light emitting source that is disposed outside of the patient's body. In yet another embodiment, the light source is disposed outside of the patient's body while administering the light therapy, and the predetermined waveband includes wavelengths sufficiently long to penetrate normal tissue overlying the internal treatment site to reach the diseased tissue without an optical fiber or a probe being invasively disposed within the patient's body.

It is also preferred that the step of ultrasonically scanning be carried out at a plurality of spaced apart times, at least a portion of which occur while the light therapy is being administered.

The step of modifying the light therapy preferably comprises the step of modifying an intensity of the light administered to the internal treatment site, a frequency with which the light is administered, and/or a duration of time during which the light is administered. It is expected that the step of modifying the light therapy can include the step of terminating administration of light to the diseased tissue, for example, if a blood flow stasis is noted in regions of the internal treatment site adjacent to normal tissue. Or, the step of modifying the light therapy can include the step of administering an additional amount of the photoreactive agent to the patient, if the change in the internal treatment site is less than desired. A desired change to the internal treatment site preferably includes either a reduction in a mass of the diseased tissue at the internal treatment site, a reduction in blood flow into the diseased tissue at the internal treatment site, and/or an indication of necrosis of the diseased tissue at the internal treatment site.

In many applications of the present invention, the diseased tissue will comprise a tumor, and the method will include the step of reviewing the change to the internal treatment site to determine an extent of an ischemic zone in the tumor, which is produced by the light therapy. It may then be appropriate to determine a rate at which an edge of the ischemic zone is propagating toward normal tissue surrounding the tumor. For some types of tumors, the light therapy will be terminated only after the ischemic zone includes a rim of normal tissue, to ensure that regrowth of the tumor does not occur.

The method may also include the step of ultrasonically scanning the internal treatment site to produce three-dimensional (3D) images of it. The 3D images of the internal treatment zone are then reviewed to determine an extent of an infarction zone produced by the light therapy.

In some cases, the method may further include the step of administering an ultrasonic contrast agent to the patient before the step of ultrasonically scanning. The ultrasonic contrast agent improves the resolution with which the internal treatment site is shown in the plurality of images.

A further aspect of the present invention is directed at a system for administering light therapy to diseased tissue at an internal treatment site within a patient's body. The system includes elements that carry out functions generally consistent with the steps of the method described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

Figure 1:
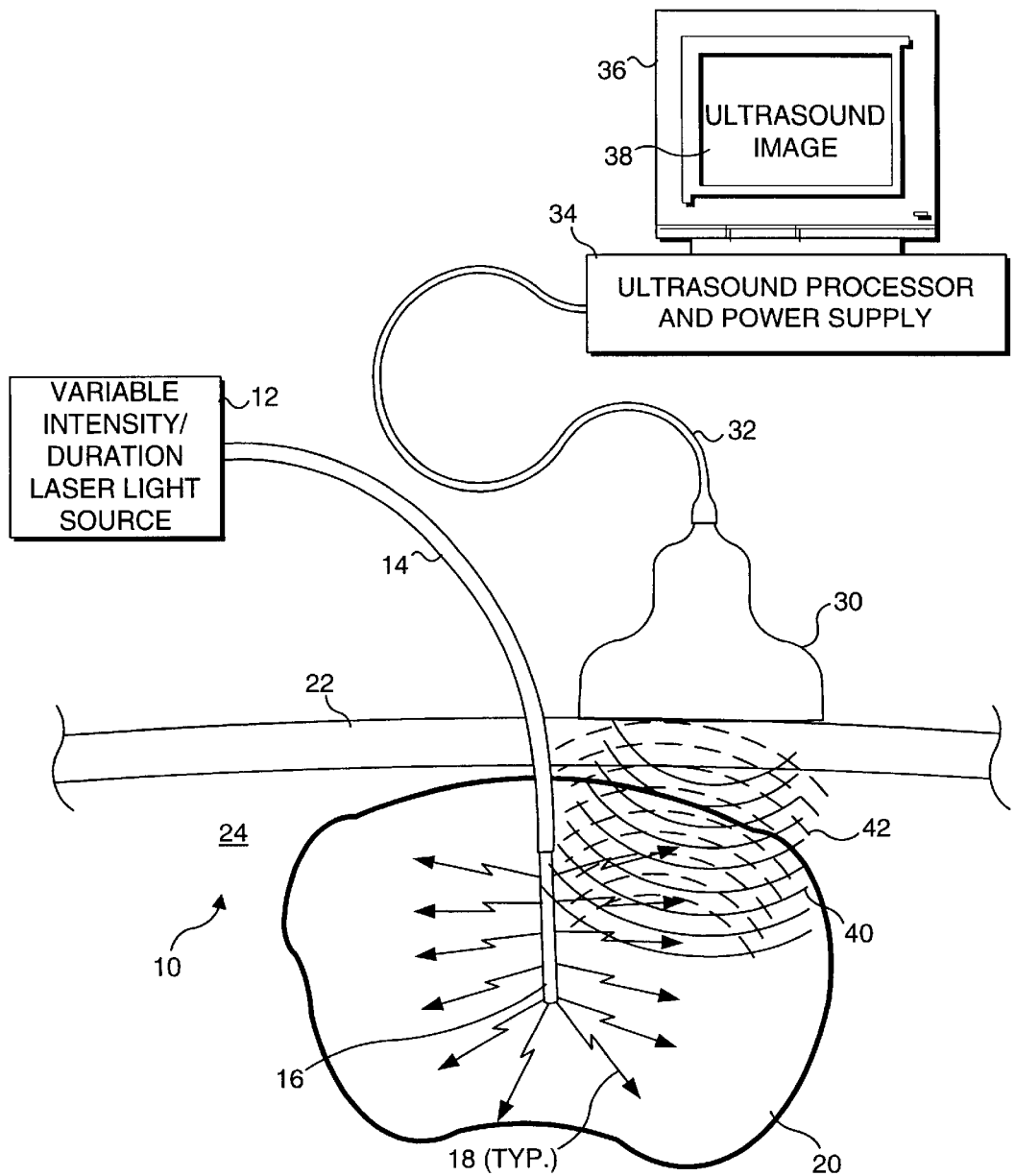
FIG. 1 is a schematic illustration showing an interstitial probe delivering light therapy to a tumor from an external laser source, and an ultrasonic probe being used to scan the tumor in real time during the light therapy, in accord with one preferred embodiment of the present invention.

As shown in FIG. 1, a system 10 is illustrated for administering PDT, while monitoring the status of the light therapy in real time, as the therapy continues. In this embodiment, a variable intensity/variable duration laser light source 12 is provided, which produces light having a predetermined waveband. To administer PDT to a patient, a photoreactive agent is administered to the patient before the light therapy begins. Suitable photoreactive agents include, but are not limited to, indocyanine green, toluidine blue, porphyrins, phthlocyanines, prodrugs such as aminolevulinic acid, chlorins, texaphyrins, purpurins, benzoporphyrins, phenothiazines, and other photoactive dyes and compounds. In addition to the photoreactive agents listed above, it is also contemplated that a targeted photoreactive agent can be used to more selectively bind to abnormal tissue at the internal treatment site. Use of such a targeted photoreactive agent is desirable, because a much lower dose of the substance can be used than would be typically be required for a non-targeted type photoreactive agent. The photoreactive agent employed can be administered via an interstitial injection, which is generally suitable for discrete lesions or tumors, or via an intravenous or intra-arterial injection. A targeted photoreactive agent typically includes antibodies that are targeted to specifically link with antigens on abnormal tissue or malignant cell organelles within a patient's body. Details relating to such targeted photoreactive agents are disclosed in commonly assigned U.S. patent applications, Ser. No. 09/078,329, filed May 13, 1998, entitled "Controlled Activation of Targeted Radionuclides;" Ser. No. 60/116,234, filed Jan. 15, 1999, entitled "Targeted Transcutaneous Cancer Therapy;" and Ser. No. 60/116,235, filed on Jan. 15, 1999, entitled "Non-invasive Vascular Therapy." The disclosure including the specification and drawings of each of these three pending patent applications is hereby specifically incorporated herein by reference.

The photoreactive agent administered to the patient that has been absorbed and/or specifically targeted at the abnormal tissue at a treatment site and consequently bound thereto will have a characteristic light absorption waveband corresponding to the predetermined waveband of light produced by variable intensity/variable duration laser light source 12. This light is conveyed from the external source through an optical fiber 14 from which the cladding has been removed at a distal end 16, so that the light from the laser source is emitted from the distal end of the optical fiber, as graphically indicated by arrows 18 in FIG. 1. Distal end 16 of optical fiber 14 is inserted into a tumor 20, having been passed through a dermal layer 22 via a surgical incision (not shown). Tumor 20 is disposed in a subdermal volume 24, internally within a patient's body.

A key aspect of the present invention is that it is particularly applicable to PDT delivered over a period of hours and possibly days, in contrast to more conventional PDT, which typically employs a relatively high intensity of light source that administers high intensity light to a treatment site for much shorter time. In connection with the present invention, it is preferable that the laser light source be adjustable in intensity and/or in the duration of pulses of light administered to the internal treatment site. While a continuously energized light source, either internal or external may be used in connection with the present invention, it is contemplated that light therapy will be administered for a prolonged period, comprising either a series of light pulses or short periods of light (from a few seconds to minutes/period) at spaced-apart intervals of time, or a continuous delivery of light at a relatively low intensity. For example, depending upon the nature of the photoreactive agents employed, the size of the tumor or diseased tissue being treated, and other variables, the duration of the PDT may be from about 1 hour to more than 24 hours. By administering PDT using a lower intensity light, or by using pulses of somewhat higher intensity of light that are delivered at spaced apart intervals of time over a prolonged duration of treatment, ischema of blood vessel vasculature that provides oxygen and nutrients to the tumor will occur, causing the tumor or diseased tissue to eventually die through anoxia. As the PDT progresses, its effect on the tumor or diseased tissue will progress as an expanding zone of infarction. This expanding infarction zone should eventually encompass the total volume of the tumor or diseased tissue.

In some instances, it may be desirable to permit the PDT to continue until the infarction zone and/or the blood vessel ischemia encompasses a rim of normal tissue surrounding the tumor, thereby insuring that the tumor does not regrow from residual diseased tissue cells that may remain viable after the PDT is terminated. Certain types of tumors are more likely to regrow in this manner, including liver tumors developed from metastases of a colon cancer. For treating such tumors, it is therefore desirable to continue the treatment until the infarction zone encompasses a rim of normal tissue surrounding the tumor.

It is also important to avoid indiscriminately damaging normal tissue by continuing PDT too long, which may well occur, without practicing the present invention. As further illustrated in FIG. 1, system 10 includes an ultrasonic transducer 30, which is coupled through a cable 32 to an ultrasound processor and power supply 34. The signal produced by ultrasound transducer 30 is processed by ultrasound processor and power supply 34, yielding an ultrasound image 38 that is displayed on a monitor 36. To produce ultrasound image 38, ultrasound transducer 30 generates ultrasonic waves 40 that propagate through dermal layer 22 and into subdermal internal volume 24. These ultrasonic waves are reflected from varying density tissue within a patient's body, producing reflected ultrasonic waves 42 that are received by the ultrasonic transducer. In response to these reflective waves, the ultrasonic transducer produces the signal produced used to create ultrasound image 38. Newer types of ultrasonic transducers enable a 3D ultrasound image to be displayed on the monitor, thereby showing the location, extent, and depth of tumor 20 at the time the ultrasonic ultrasound image was produced.

By studying ultrasound images in real time, it is possible to monitor the progress of PDT within tumor 20 and thus to determine the effect of the PDT in making decisions about modifying the therapy. For example, variable intensity/variable duration laser light source 12 can be adjusted to change the intensity of the light that it produces, and/or to increase or shorten the duration of each interval of time during which it produces light, and the frequency of such intervals during which the light is administered through optical fiber 14 to tumor 20. In addition, the ultrasound image can be evaluated to determine when or if it is necessary to administer another bolus or dose of the photoreactive agent to the patient, since the effect of the PDT will diminish over time as the concentration of the photoreactive agent within tumor 20 decreases.

To better monitor changes within tumor 20 as a result of PDT, it is contemplated that an initial ultrasound image will be produced using ultrasound transducer 30 prior to initiating administration of light therapy through optical fiber 14. This initial ultrasound image will serve as a baseline image against which changes in the tumor as a result of the ongoing PDT are evaluated. Alternatively, a quasi-baseline image can be produced by ultrasonically scanning the tumor shortly after beginning to administer light to tumor 20, since the changes will be minimal at that point during the therapy.

It should also be noted that ultrasonic transducer 30 can initially be employed to locate an internal treatment site where tumor 20 or other diseased tissue is disposed by evaluating ultrasound image 38. By locating the position, extent, and the volume of the tumor, various parameters related to administration of PDT to the tumor or other diseased tissue can be determined prior to beginning the treatment. Knowing the location of the tumor will help in positioning the light source to accurately administer light to the tumor.

Figure 2:
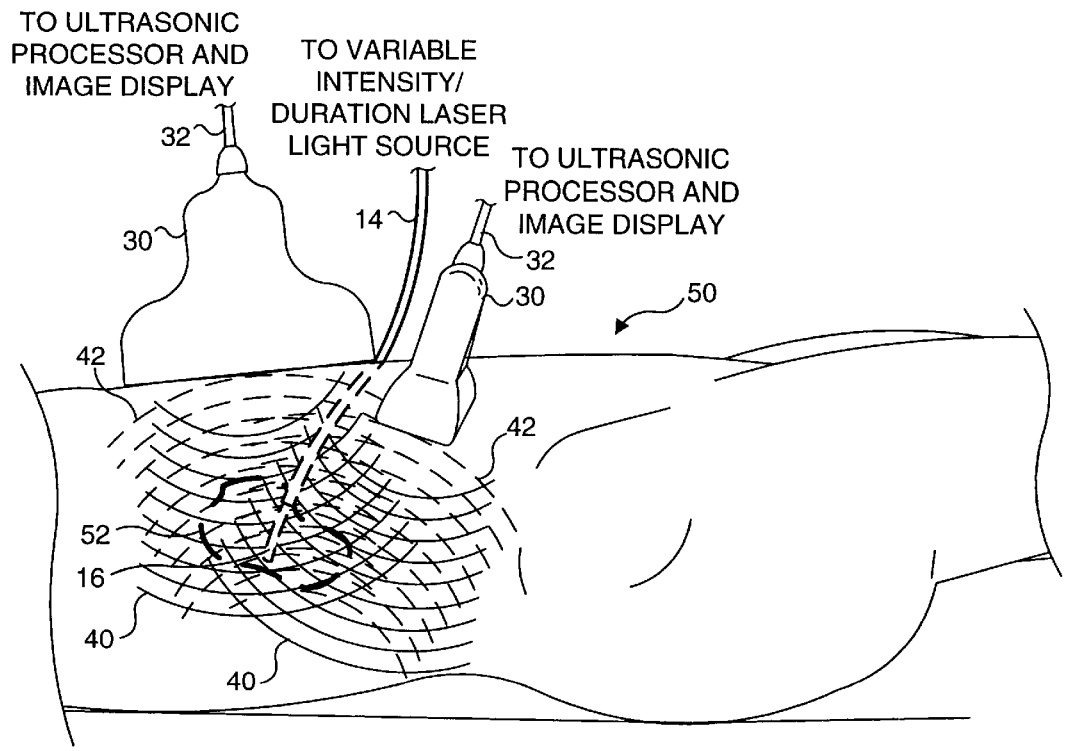
FIG. 2 is schematic illustration showing how a 3D ultrasonic scan is made of an internal tumor from different positions on a patient's body.

Ultrasonic transducer 30 can be repositioned to produce additional ultrasound images of an internal tumor 52 within a patient's body 50, since by repositioning the ultrasound transducer, a different viewpoint is achieved that more clearly identifies the scope and condition of the internal treatment site and the results of the PDT. Alternatively, two ultrasonic transducers 30, as shown in FIG. 2, should also help to more accurately define the position of tumor 52, its extent, and volume, for purposes of emplacement of optical fiber 14 to administer light to the tumor. In addition, imaging the tumor from different positions to better reveal the effects of the PDT, as shown in FIG. 2, should enable a medical practitioner to more conclusively evaluate the changes in the tumor or diseased tissue as a result of PDT, thereby enabling a more accurate evaluation of the PDT to be obtained.

It should be noted that the concept of "modifying the PDT" is intended to encompass termination of the PDT, if changes to an internal treatment site determined by evaluating the ultrasound images indicate that the tumor or diseased tissue has been substantially destroyed. Termination of the PDT at an appropriate point and time should avoid harmful effects of the therapy on normal tissue within the patient's body that might otherwise occur.

Figure 3:
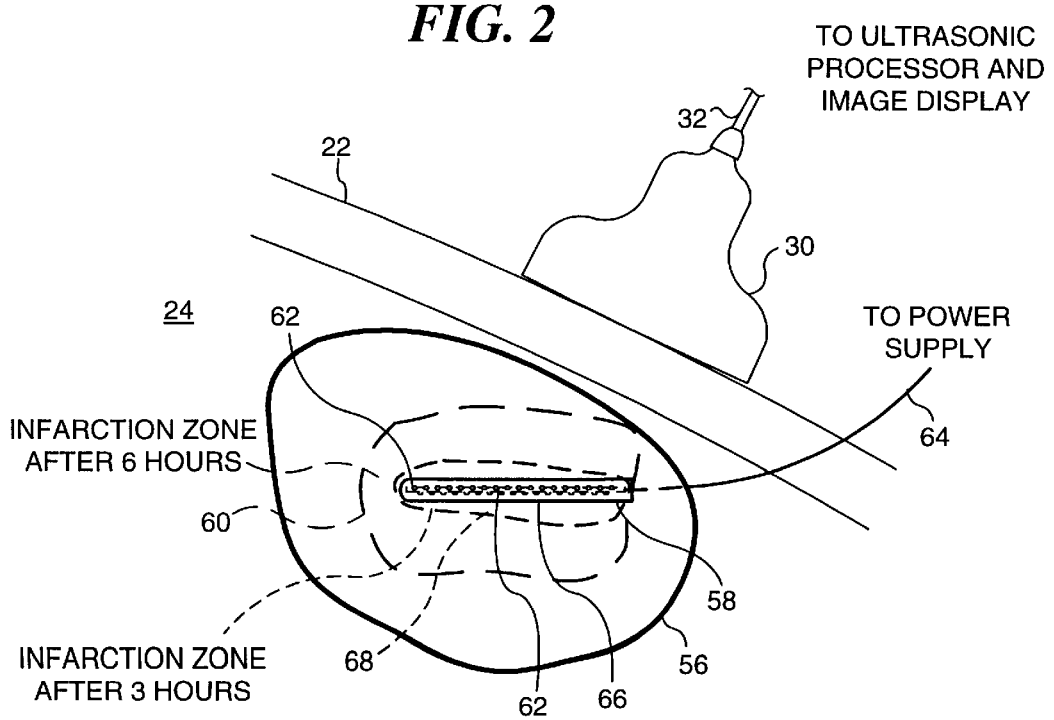
FIG. 3 is a schematic illustration showing an interstitial probe that includes a plurality of LEDs being used to administer light therapy to a tumor that is being ultrasonically scanned.

FIG. 3 illustrates a second embodiment of the present invention in which a tumor 56 is being administered light therapy using an implanted light probe 58. In light probe 58, a flexible substrate 62 includes a plurality of conductive traces (not shown) that convey electrical current to a plurality of light emitting diodes (LEDs) or other light sources. The electrical current is conveyed from an external power supply (not shown) through a lead 64, which extends through dermal layer 22 and outside the patient's body (or extends to an internal power supply—not shown). A plurality of light sources are enclosed within a flexible biocompatible and optically transparent envelope 66 so that the light emitted by the light sources is incident on the diseased and abnormal tissue within tumor 56. An appropriate photoreactive agent, for example one of the various targeted or non-targeted photoreactive agents listed above, is administered to the patient. Ultrasonic transducer 30 is again employed to produce ultrasound images that enable the medical practitioner to determine changes in tumor 56. For example, an infarction zone 68 illustrated by a dash line around light probe 58, is developed within tumor 56 and shows the result of administering PDT for three hours. Infarction zone 68 is evident in the ultrasound image produced by ultrasonic probe 30 and can be compared to a later ultrasound image produced after PDT has been administered for six hours, showing an infarction zone 60, which is substantially larger in volume than infarction zone 68. Again, by monitoring still further changes in tumor 56 in real time, following additional PDT, the medical practitioner can terminate delivery of PDT to the internal treatment site after the infarction zone has reached the limits of tumor 56, thereby minimizing any adverse impact on the surrounding normal tissue. In addition, appropriate changes in the PDT, such as changes in the intensity of light delivered by light probe 58, or the duration of the intervals of time it is energized during the PDT can be controlled as a function of the changes in the internal treatment site observed in the ultrasound images. As appropriate, additional photoreactive agent can be administered, as described above in connection with the first embodiment.

Figure 4:
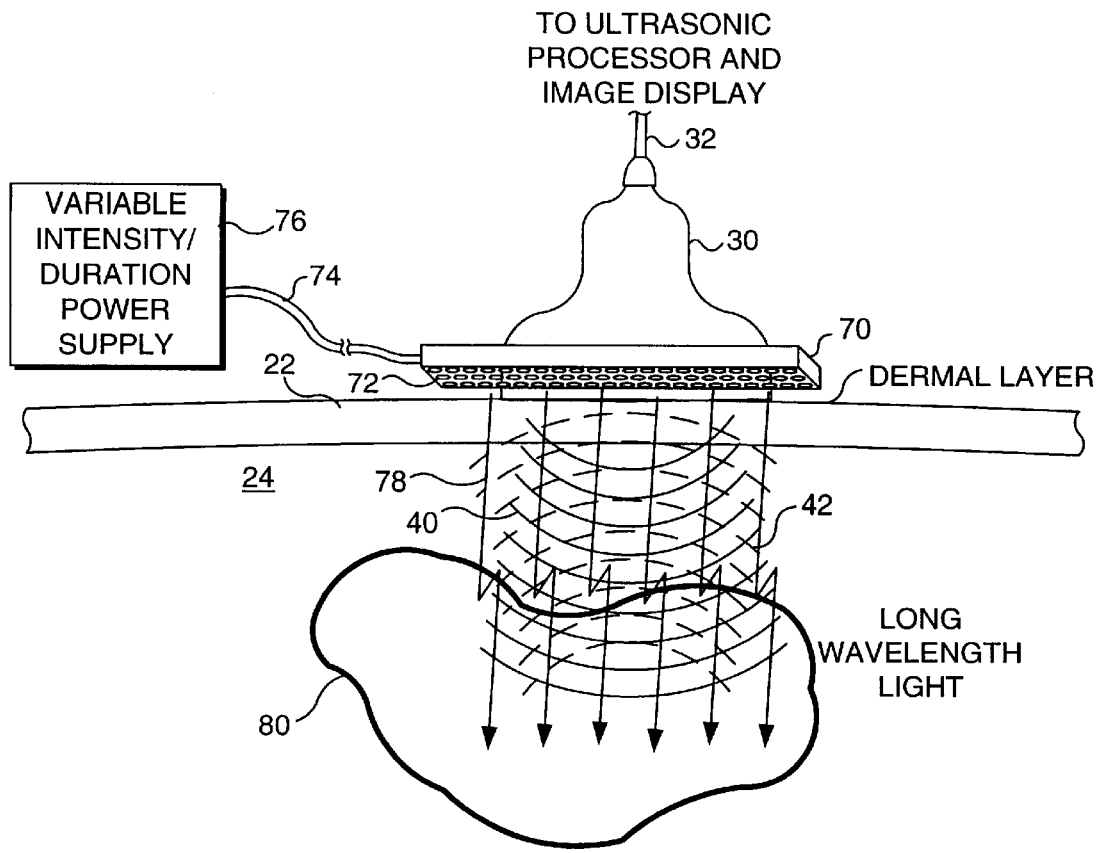
FIG. 4 is a schematic illustration showing an external array of LEDs used to transdermally illuminate a tumor that is being ultrasonically scanned.

Referring now to FIG. 4, a third embodiment of the present invention is shown in which an external array 70 of LEDs 72 that emit relatively long wavelength light, for example, in a waveband that includes wavelengths greater than 700 nm, is used to administer light therapy to an internal tumor 80. LEDs 72 are energized with electrical current provided through a cable 74 from a variable intensity/variable duration power supply 76, which can be selectively controlled to change the current supplied to the LEDs and to control the spaced-apart times or intervals during which the LEDs are energized when administering PDT. As shown in FIG. 4, ultrasonic transducer 30 is disclosed immediately behind external array 70 and produces ultrasound waves 40 that propogate into subdermal internal volume 24 through dermal layer 22. Tumor 80 reflects ultrasonic waves 40, producing reflected ultrasonic waves 42 that are received by ultrasonic transducer 30, which produces an output signal in response thereto, for use in imaging tumor 80. The light produced by array 70 has a sufficiently long wavelength to readily penetrate into the body and into tumor 80, where it activates a photoreactive agent having a characteristic absorption waveband corresponding to the waveband of the relatively long wavelength light produced by LEDs 72.

Figure 6:
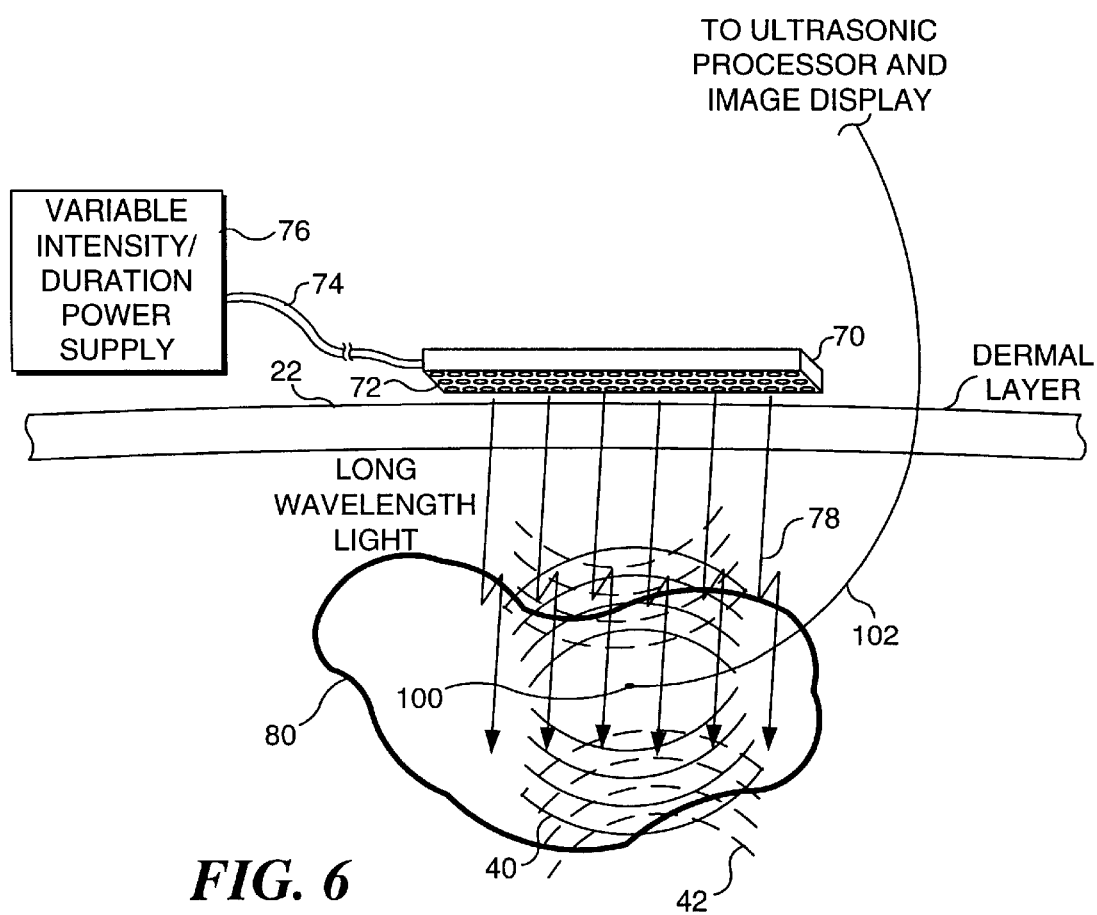
FIG. 6 is a schematic illustration showing an external array of LEDs used to transdermally illuminate a tumor that is being ultrasonically scanned with a Doppler wire ultrasonic probe.

Yet another embodiment of the present invention, which is generally similar to that shown in FIG. 4 is illustrated in FIG. 6, except that instead of using an ultrasonic transducer 30, a Doppler ultrasound-tipped transducer 100 is inserted into tumor 80 and energized with a signal that carried by a lead 102 from an external ultrasonic processor and image display (not shown). Doppler ultrasonic-tipped transducer 100 comprises, for example, a 5.5–10.0 MHz frequency agile transducer that is capable of full spectral and color Doppler imaging in addition to two-dimensional (2D) imaging. Doppler ultrasonic-tipped transducer 100 produces ultrasonic waves 40 and receives reflected ultrasonic waves 42, generally as described above, for producing a signal used in creating the ultrasound images that are 2D and include color to illustrate Doppler flow, velocity, and hemodynamics in surrounding blood vessels. As described above, the system shown in FIG. 6 also uses array 70 to administer relatively long wavelength light 78 that readily penetrate through dermal layer 22 and into tumor 80, at the internal treatment site within the patient's body. Alternatively, ultrasonic transducer 100 can also be used with either light probe 58, or optical fiber 14, both of which administer light interstitially to a tumor.

Figure 5:
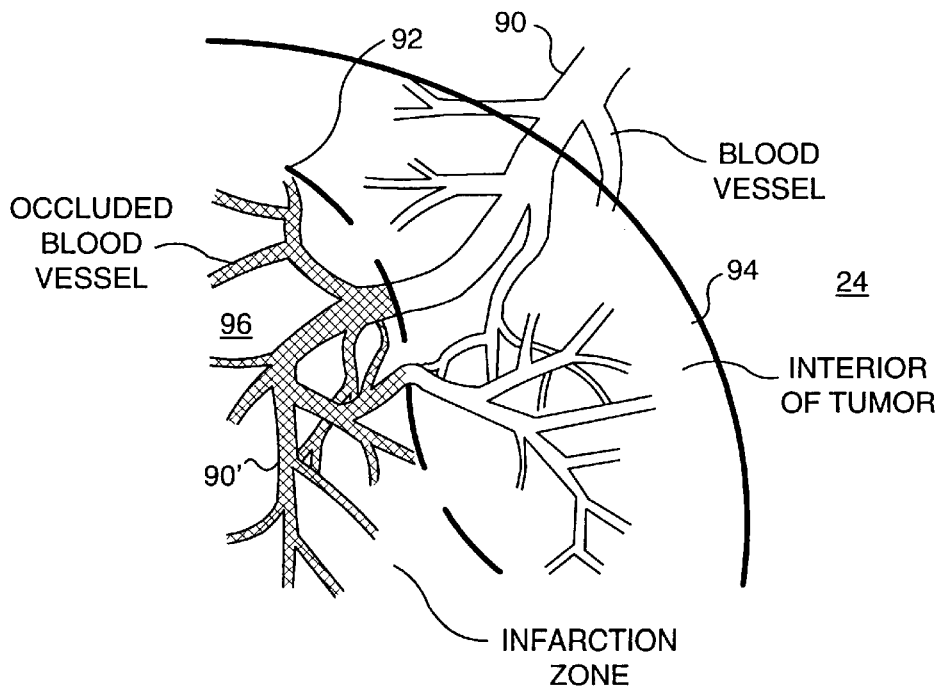
FIG. 5 is a greatly enlarged portion of an internal tumor showing a portion of a blood vessel that has been occluded by PDT within an infarction zone of the tumor.

As noted above, an important aspect of the present invention is the ability it provides the medical practitioner to monitor in real time the effect of PDT in destroying diseased tissue and in creating an infarction zone within a tumor. FIG. 5 illustrates how PDT delivered over an extended period of time in accordance with the present invention causes ischemia of a blood vessel 90, which normally provides oxygenated blood to a tumor 94. In this figure, no attempt has been made to illustrate the entire extent of blood vessel 90, but instead, it is graphically illustrated without showing the terminal capillaries that spread throughout the interior of tumor 94. It should be noted that a contrast agent can be administered to a patient to improve the contrast in the ultrasonic images made in accord with the present invention, particularly to improve the contrast with which blood flow in vessels is depicted in such images. Appropriate contrast agents suitable for this purpose are well known to those of ordinary skill in producing ultrasound images.

As a result of administering of PDT to tumor 94, an infarction zone 96 develops within the interior of the tumor and this infarction zone has a border indicated by a dash line 92. Inside infarction zone 96, which has been produced by administering PDT over an extended period of time, ischemia of blood vessel 90 has occluded blood flow through the blood vessel. The ischemic portion of blood vessel 90 is indicated by the cross-hatched area 90'. As additional PDT is delivered, the volume of infarction zone 96 and the area of the ischemic portion of the blood vessels supplying the tumor continue to increase. In response to the infarction zone approaching the limits of tumor 94 as shown in the ultrasound images, a medial practitioner would likely reduce the intensity of the light administered, and at appropriate time, would terminate administration of the PDT to tumor 94.

It will be evident that the ability to monitor the progress of PDT and its effect on a tumor or other diseased tissue greatly facilitates control of the therapy, enabling the medical practitioner to fine tune the administration of PDT and to terminate it at an appropriate time. Without benefit of the ultrasound images produced in accord with the present invention, control of PDT is generally inexact, and potentially dangerous to a patient if the PDT is not terminated once the diseased tissue has been destroyed. The present invention enables control of the light therapy, thereby avoiding possible harm to normal tissue.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for administering light therapy to diseased tissue at an internal treatment site within a patient's body that enables the light therapy to be modified in response to a condition of the internal treatment site, comprising the steps of:
   (a) providing a light source that emits light within a predetermined waveband;
   (b) administering a photoreactive agent to the patient, said photoreactive agent having a characteristic light absorption waveband corresponding to the predetermined waveband in which light is emitted by the light source;
   (c) administering light to the diseased tissue with the light source over an extended perod of time;
   (d) ultrasonically scanning the internal treatment site at a plurality of times to produce a corresponding plurality of images, each image indicating a condition of the internal treatment site, said plurality of times including:
      (i) before the onset of administering the light, to produce a baseline image of the diseased tissue at the internal treatment site, prior to the internal treatment site experiencing any effect from the light subsequently administered thereto; and
      (ii) at least one time after an onset of administering the light; and
   (e) detecting changes in the condition of the internal treatment site by comparing the baseline image with a subsequent image made a substantial time after the onset of administering the light to the diseased tissue at the internal treatment site.

2. The method of claim 1, wherein the step of ultrasonically scanning includes the step of scanning the internal treatment site before a substantial amount of light has been administered, to produce a quasi-baseline image of the diseased tissue at the internal treatment site before the diseased tissue is substantially affected by the light.

3. The method of claim 2, wherein the step of detecting the changes in the internal treatment site includes the step of comparing the quasi-baseline image with a subsequent image made a substantial time after the onset of administering the light to the diseased tissue at the internal treatment site.

4. The method of claim 1, wherein the light source comprises a probe in which at least one light emitting source is disposed, said probe being adapted to be inserted interstitially within the diseased tissue.

5. The method of claim 1, wherein the light source comprises an optical fiber having a distal end adapted to be interstitially inserted into the diseased tissue and to convey light into the treatment site from a light emitting source that is disposed outside of the patient's body, at a proximal end of the optical fiber.

6. The method of claim 1, wherein the light source is disposed outside the patient's body while administering the light therapy, and wherein the predetermined waveband includes wavelengths sufficiently long to penetrate normal tissue overlying the internal treatment site, to reach the diseased tissue.

7. The method of claim 1, wherein the step of ultrasonically scanning is carried out at a plurality of spaced-apart times, and wherein at least a portion of said spaced-apart times occur while the light therapy is being administered.

8. The method of claim 1, further comprising the step of modifying the light therapy in response to a change in the internal treatment site that was detected.

9. The method of claim 8, wherein the step of modifying the light therapy comprises the step of modifying at least one of:
   (a) an intensity of the light administered to the internal treatment site;
   (b) a frequency with which the light is administered
   (c) a duration during which the light is administered by the light source within each of a series of intervals of time; and
   (d) administration of the light, by terminating the administration thereof.

10. The method of claim 8, wherein the step of modifying the light therapy includes the step of terminating administration of light to the diseased tissue if a blood flow stasis is noted in regions of the internal treatment site adjacent to normal tissue.

11. The method of claim 8, wherein the step of modifying the light therapy includes the step of administering an additional dose of the photoreactive agent to the patient, if the change in the internal treatment site is less than desired.

12. The method of claim 11, wherein a desired change to the treatment site includes at least one of:
   (a) a reduction in a mass of the diseased tissue at the internal treatment site;
   (b) a reduction in blood flow into the diseased tissue at the internal treatment site; and
   (c) an indication of necrosis of the diseased tissue at the internal treatment site.

13. The method of claim 1, wherein the diseased tissue comprises a tumor, further comprising the step of reviewing the changes to the internal treatment site to determine an extent of an ischemic zone in the tumor, said ischemic zone being produced by the light therapy.

14. The method of claim 13, wherein the step of reviewing includes the step of determining a rate at which an edge of the ischemic zone is advancing toward normal tissue surrounding the tumor.

15. The method of claim 13, further comprising the step of terminating the light therapy only after the ischemic zone includes a rim of normal tissue to ensure that regrowth of the tumor does not occur.

16. The method of claim 1, further comprising the step of ultrasonically scanning the patient's body to determine at least one of a location and an extent of the diseased tissue, for purposes of directing the administration of the light therapy thereto.

17. The method of claim 16, further comprising the step of positioning an ultrasonic probe internally within the patient's body to carryout the step of ultrasonically scanning the internal treatment site.

18. The method of claim 1, further comprising the step of administering an ultrasonic contrast agent to the patient before the step of ultrasonically scanning, said ultrasonic contrast agent improving resolution with which the internal treatment site is shown in the plurality of images.

19. A method for administering light therapy to diseased tissue at an internal treatment site within a patient's body over an extended period of time that enables the light therapy to be modified in response to a condition of the internal treatment site, comprising the steps of:

(a) positioning an interstitial light source within the diseased tissue, said interstitial light source emitting light within a predetermined waveband;

(b) administering a photoreactive agent to the patient, said photoreactive having a characteristic light absorption waveband corresponding to the predetermined waveband in which light is emitted by the interstitial light source;

(c) administering light to the diseased tissue at the internal treatment site with the interstitial light source over the extended period of time;

(d) at a plurality of times, including a time before the light is administered to the internal treatment site and a time substantially after administration of the light to the internal treatment site has begun, ultrasonically scanning the internal treatment site to produce a corresponding plurality of images, each image indicating at least one of:

(i) a volume of the diseased tissue;

(ii) a boundary between the diseased tissue and normal tissue; and (iii) a blood flow pattern at the internal treatment site; and (e) detecting changes in the internal treatment site by comparing an image of the internal treatment site made at a time substantially after the light therapy has begun, with an image made at an earlier time.

20. The method of claim 19, further comprising the step of modifying the light therapy in response to a change in the internal treatment site that was detected.

21. The method of claim 20, wherein the step of modifying comprises the step of repositioning the interstitial light source to selectively treat diseased tissue identified as viable after the light has been administered to the diseased tissue at the internal treatment site for the extended period of time.

22. The method of claim 20, wherein the step of modifying comprises the step of changing an intensity of the light administered to the diseased tissue by the interstitial light source.

23. The method of claim 20, wherein the step of modifying comprises the step of terminating administration of the light to the diseased tissue.

24. The method of claim 20, wherein the step of modifying comprises the step of administering an additional dose of the photoreactive agent to the patient.

25. The method of claim 20, wherein the step of modifying comprises the step of changing a duration of a each of a plurality of time intervals in which the interstitial light source administers light to the diseased tissue.

26. The method of claim 20, wherein the diseased tissue comprises a tumor, and wherein the step of modifying is carried out at least when the step of detecting changes indicates that a zone of blood flow reduction within the tumor caused by the light therapy is approaching a boundary of the tumor.

27. The method of claim 20, wherein the diseased tissue comprises a tumor, and wherein the step of modifying comprises the step of terminating administration of the light to the diseased tissue at the internal treatment site when the step of detecting changes indicates that an ischemic zone in the tumor includes a rim of normal tissue surrounding the tumor.

28. The method of claim 19, wherein the interstitial light source comprises one of a light emitting probe that includes a light emitting source, and an optical fiber coupled to a light emitting source disposed outside the patient's body.

29. The method of claim 19, wherein the step of ultrasonically scanning is implemented at spaced apart times, and wherein an interval between successive ultrasonic scans of the internal treatment site is empirically determined.

30. The method of claim 19, further comprising the step of administering an ultrasonic contrast agent to improve a resolution with which the treatment site is depicted in the plurality of images.

31. The method of claim 19, wherein the step of ultrasonically scanning comprises the step of ultrasonically scanning at substantially different points on the patient's body to produce ultrasound images from the different point.

32. The method of claim 19, wherein the step of administering light to the diseased tissue at the internal treatment site is permitted to continue while the plurality of images indicate a substantial portion of the diseased tissue remains viable.

33. The method of claim 19, wherein the extended period is at least one hour in duration.

34. The method of claim 19, wherein the extended period of time is more than 12 hours in duration.

35. The method of claim 19, further comprising the step of positioning an ultrasonic transducer internally within the patient, and wherein the step of ultrasonically scanning is implemented using said ultrasonic transducer that is internally positioned.

36. The method of claim 19, further comprising the step of ultrasonically scanning the patient's body to determine at least one of a location and an extent of the diseased tissue, for purposes of directing the administration of the light therapy thereto.

37. A system for administering light therapy to diseased tissue at an internal treatment site within a patient's body, comprising:

(a) a light source that produces light within a predetermined waveband, said light source being adapted to be used externally of a patient's body, wherein the light produced by the light source within the predetermined waveband includes light having a sufficiently long wavelength to penetrate tissue overlying the internal treatment site;

(b) a photoreactive agent having a characteristic light absorption waveband corresponding to the predetermined waveband of the light source, said photoreactive agent destroying the diseased tissue when activated by light from the light source;

(c) an ultrasonic transducer that produces ultrasonic waves and receives reflected waves when the ultrasonic waves are reflected from the diseased tissue within a patient's body, said ultrasonic transducer producing an output signal in response to the reflected waves; and (d) a display coupled to the ultrasonic transducer to receive the output signal, said display being adapted to produce a plurality of images of the diseased tissue within a patient's body during administration of the light therapy to enable changes in the diseased tissue caused by the light therapy to be detected by comparison of images made at different times.

38. The system of claim 37, wherein the ultrasonic transducer is adapted to be disposed and used externally of a patient's body to produce the plurality of images.

39. The system of claim 37, wherein the ultrasonic transducer is adapted to be positioned internally within a patient's body to produce the plurality of images.

40. The system of claim 39, wherein the ultrasonic transducer comprises a Doppler type transducer and is adapted to produce color ultrasound images on the display.

41. The system of claim 37, wherein the light source comprises an interstitial probe that is adapted to be inserted internally within a patient's body.

42. The system of claim 37, wherein the light source comprises a laser and an optical fiber adapted to convey light produced by the laser into a patient's body, to administer the light to the diseased tissue.

43. A method for administering light therapy to diseased tissue at an internal treatment site within a patient's body and enabling the light therapy to be modified in response to a condition of the internal treatment site, comprising the steps of:

(a) providing a light source disposed outside the patient's body while administering the light therapy, said light source emitting light within a predetermined waveband; said predetermined waveband including wavelengths sufficiently long to penetrate normal tissue overlying the internal treatment site, to reach the diseased tissue;

(b) administering a photoreactive agent to the patient, said photoreactive agent having a characteristic light absorption waveband corresponding to the predetermined waveband in which light is emitted by the light source;

(c) administering light to the diseased tissue with the light source over an extended period of time;

(d) at a plurality of times, including at least one time after an onset of administering the light, ultrasonically scanning the internal treatment site to produce a corresponding plurality of images, each image indicating a condition of the internal treatment site; and (e) detecting changes in the condition of the internal treatment site by comparing an image of the internal treatment site made at a time after the onset of administering the light, with an image made at an earlier time.

44. A method for administering light therapy to a tumor at an internal treatment site within a patient's body and enabling the light therapy to be modified in response to a condition of the internal treatment site, comprising the steps of:

(a) providing a light source that emits light within a predetermined waveband;

(b) administering a photoreactive agent to the patient, said photoreactive agent having a characteristic light absorption waveband corresponding to the predetermined waveband in which light is emitted by the light source;

(c) administering light to the diseased tissue with the light source over an extended period of time;

(d) at a plurality of times, including at least one time after an onset of administering the light, ultrasonically scanning the internal treatment site to produce a corresponding plurality of images, each image indicating a condition of the internal treatment site;

(e) detecting changes in the condition of the internal treatment site by comparing an image of the internal treatment site made at a time after the onset of administering the light, with an image made at an earlier time;

(f) reviewing the changes to the internal treatment site to determine an extent of an ischemic zone in the tumor, said ischemic zone being produced by the light therapy; and (g) terminating the light therapy once a desired extent of the ischemic zone has been achieved.

* * * * *